US011344657B2

(12) United States Patent
Biewer et al.

(10) Patent No.: US 11,344,657 B2
(45) Date of Patent: May 31, 2022

(54) DIALYSIS SOLUTION WASTE MINIMIZATION SYSTEMS AND METHODS

(71) Applicant: Fresenius Medical Care Holdings, Inc., Waltham, MA (US)

(72) Inventors: John A. Biewer, Waltham, MA (US); Kulwinder S. Plahey, Martinez, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 155 days.

(21) Appl. No.: 17/016,999

(22) Filed: Sep. 10, 2020

(65) Prior Publication Data

US 2020/0405940 A1 Dec. 31, 2020

Related U.S. Application Data

(63) Continuation of application No. 15/711,114, filed on Sep. 21, 2017, now Pat. No. 10,806,844.

(51) Int. Cl.
*A61M 1/28* (2006.01)
*A61M 1/36* (2006.01)
*A61M 5/36* (2006.01)
*A61M 5/44* (2006.01)

(52) U.S. Cl.
CPC ............ *A61M 1/284* (2014.02); *A61M 1/287* (2013.01); *A61M 1/288* (2014.02); *A61M 1/369* (2013.01); *A61M 5/365* (2013.01); *A61M 5/445* (2013.01); *A61M 2205/3368* (2013.01); *A61M 2205/3379* (2013.01); *A61M 2205/3393* (2013.01); *A61M 2205/36* (2013.01)

(58) Field of Classification Search
CPC ...... A61M 1/284; A61M 1/287; A61M 1/288; A61M 1/369; A61M 5/365; A61M 5/445; A61M 2205/3368; A61M 2205/3379; A61M 2205/3393; A61M 2205/36; A61M 1/0019; A61M 1/14; A61M 1/16; A61M 1/1601; A61M 1/165; A61M 1/1656; A61M 1/166; A61M 1/1664; A61M 1/1668; A61M 1/28; A61M 1/282; A61M 2205/12; A61M 2205/18; A61M 2205/3331; A61M 2205/3334
See application file for complete search history.

(56) References Cited

U.S. PATENT DOCUMENTS

| | | | | |
|---|---|---|---|---|
| 4,229,299 A | * | 10/1980 | Savitz | ................. A61M 1/1662 417/477.13 |
| 2002/0045851 A1 | * | 4/2002 | Suzuki | .................... A61M 5/44 604/113 |

* cited by examiner

*Primary Examiner* — Pranav N Patel
(74) *Attorney, Agent, or Firm* — KDB

(57) ABSTRACT

Dialysis machines and methods for operating dialysis machines (e.g., peritoneal dialysis machines) may include delivering dialysate to a patient and detecting a temperature of a volume of the dialysate, an air content of the dialysate volume, or another condition, or combinations thereof, wherein the detected temperature of the dialysate volume is compared to a predetermined maximum temperature, the detected air content of the dialysate volume is compared to a predetermined maximum air content and the detected other condition generates a signal. The volume of dialysate may be diverted in response to the detected temperature exceeding the predetermined maximum temperature, the air content exceeding the predetermined maximum air content, or the other condition generated signal, or combinations thereof.

23 Claims, 7 Drawing Sheets

DIALYSIS SOLUTION WASTE MINIMIZATION SYSTEMS AND METHODS

CROSS-REFERENCE TO RELATED APPLICATIONS

The present application is a continuation of co-pending U.S. patent application Ser. No. 15/711,114, filed Sep. 21, 2017, entitled "Dialysis Solution Waste Minimization Systems and Methods," the contents of which application are expressly incorporated by reference herein.

FIELD OF THE DISCLOSURE

The disclosure generally relates to dialysis machines, and more particularly to dialysis solution waste minimization systems and methods.

BACKGROUND OF THE INVENTION

Dialysis machines are known for use in the treatment of renal disease. The two principal dialysis methods are hemodialysis (HD) and peritoneal dialysis (PD). During hemodialysis, the patient's blood is passed through a dialyzer of a hemodialysis machine while also passing dialysate through the dialyzer. A semi-permeable membrane in the dialyzer separates the blood from the dialysate within the dialyzer and allows diffusion and osmosis exchanges to take place between the dialysate and the blood stream. During peritoneal dialysis, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. Automated peritoneal dialysis machines, called PD cyclers, are designed to control the entire peritoneal dialysis process so that it can be performed at home, usually overnight, without clinical staff in attendance.

A dialysis machine, such as a peritoneal dialysis machine, may include bags containing a fluid, e.g., a dialysate for patient infusion. In peritoneal dialysis machines, for example, tubing as fluid lines are inserted into an abdomen of a patient for flowing fresh dialysate and removing used dialysate, waste, and excess fluid. In bags containing fresh dialysate, a volume of air (e.g., an air content) may also be present, for example, due to fill levels, osmosis, and/or other conditions. If the dialysis machine draws a combination of dialysate and air content (e.g., air bubbles) from one of the bags or elsewhere in the system, the dialysis machine may deliver less than the prescribed volume of dialysate to the patient over the course of the treatment and/or a potentially painful build-up of excess air in the patient may result. Additionally, dialysate flow may change during treatment, which may result in dialysate being overheated and undeliverable at that temperature to the patient. Other events during treatment may occur as well, which may affect the delivery of dialysate. In some embodiments, a dialysis machine may react to these conditions by alerting the patient via an alarm or other notification, and may pause or even stop the treatment. In some embodiments, in order to continue treatment the dialysis machine may automatically purge the dialysate or combination of dialysate and air content, for example, to a drain. Fresh dialysate that is drained due to air content volume or temperature, or another condition, may waste an unacceptable amount of dialysate, and may result in the patient not receiving a full prescribed treatment or a treatment time being unnecessarily extended. When a patient receives less than 90% of a dialysate treatment, it may be considered ineffective.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a method for a dialysis treatment by a dialysis machine may include delivering a volume of dialysate with the dialysis machine to a patient, and detecting a temperature of the dialysate volume, an air content of the dialysate volume, or another condition, or combinations thereof, wherein the detected temperature of the dialysate volume is compared to a predetermined maximum temperature, the detected air content of the dialysate volume is compared to a predetermined maximum air content, or the detected other condition generates a signal, or combinations thereof. The method may further include diverting the volume of dialysate in response to the detected temperature exceeding the predetermined maximum temperature, the air content exceeding the predetermined maximum air content, or the other condition generated signal, or combinations thereof. The method may further include transferring the diverted volume of dialysate to the patient at a later point during the dialysis treatment.

According to an exemplary embodiment of the present disclosure, a dialysis system for conducting a dialysis treatment may include a dialysis machine for transferring dialysate to a patient. The dialysis machine may be configured to flow the dialysate, and detect for a volume of the dialysate, a temperature of the dialysate volume, an air content of the dialysate volume, or another condition, or combinations thereof, wherein the detected temperature of the dialysate volume is compared to a predetermined maximum temperature, the detected air content of the dialysate volume is compared to a predetermined maximum air content, or the detected other condition generates a signal, or combinations thereof. The dialysis machine may further be configured to divert the volume of dialysate in response to the detected temperature exceeding the predetermined maximum temperature, the air content exceeding the predetermined maximum air content, or the other condition generated signal, or combinations thereof. The dialysis machine may further be configured to transfer the diverted volume of dialysate to the patient at a later point during the dialysis treatment.

According to an exemplary embodiment of the present disclosure, a method for minimizing dialysate waste during treatment by a dialysis system may include detecting (i) a temperature of a dialysate volume, wherein the detected temperature of the dialysate volume is compared to a predetermined maximum temperature. The method may further include detecting (ii) an air content of the dialysate volume, wherein the detected air content of the dialysate volume is compared to a predetermined maximum air content. The method may further include detecting (iii) another condition of the treatment, wherein the detected other condition generates a signal. The method may further include detecting any combinations of (i), (ii) and (iii). The method may further include diverting the volume of dialysate in response to (vi) the detected temperature exceeding the predetermined maximum temperature, (v) the air content exceeding the predetermined maximum air content or (vi) the other condition generated signal. The method may further include diverting in response to any combinations of (iv), (v) and (vi). In various of the foregoing and other embodiments of the present disclosure, the other condition may include detecting a new treatment set of a cartridge and tubing, priming the tubing, or detecting a treatment event alarm or flow stop, or combinations thereof.

In various of the foregoing and other embodiments of the present disclosure, the volume of dialysate may be delivered from a dialysate bag to the dialysis machine via a heater bag, the heater bag being disposable on a top surface of the dialysis machine, such that the volume of dialysate is heatable by batch in the heater bag. In various of the foregoing and other embodiments of the present disclosure, the volume of dialysate may be delivered from a dialysate bag to the dialysis machine via a warmer pouch. The warmer pouch is in-line with the dialysis machine, the warmer pouch being configured such that dialysate is continuously flowable through the warmer pouch.

In various of the foregoing and other embodiments of the present disclosure, the diverted volume of dialysate may be transferred to the patient at a later point during the dialysis treatment. The diverted volume of dialysate may be deliverable to the patient after delivery of dialysate from all dialysate bags. The diverted volume of dialysate may be deliverable to the patient in response to the detected temperature being below the predetermined maximum temperature, the air content being below the predetermined maximum air content, or the other condition is acceptable, or combinations thereof.

In various of the foregoing and other embodiments of the present disclosure, the volume of dialysate may be diverted to a dialysate container. The dialysate container may be an additional holding reservoir, an unused dialysate bag, or a used dialysate bag, or combinations thereof. In various of the foregoing and other embodiments of the present disclosure, the dialysis machine may be configured to actively cool the diverted volume of dialysate. In various of the foregoing and other embodiments of the present disclosure, the dialysis machine may be configured to provide an active measurement of the diverted volume of dialysate. In various of the foregoing and other embodiments of the present disclosure, the other condition may include detecting a new treatment set of a cartridge and tubing, priming the tubing, or detecting a treatment event alarm or flow stop, or combinations thereof.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
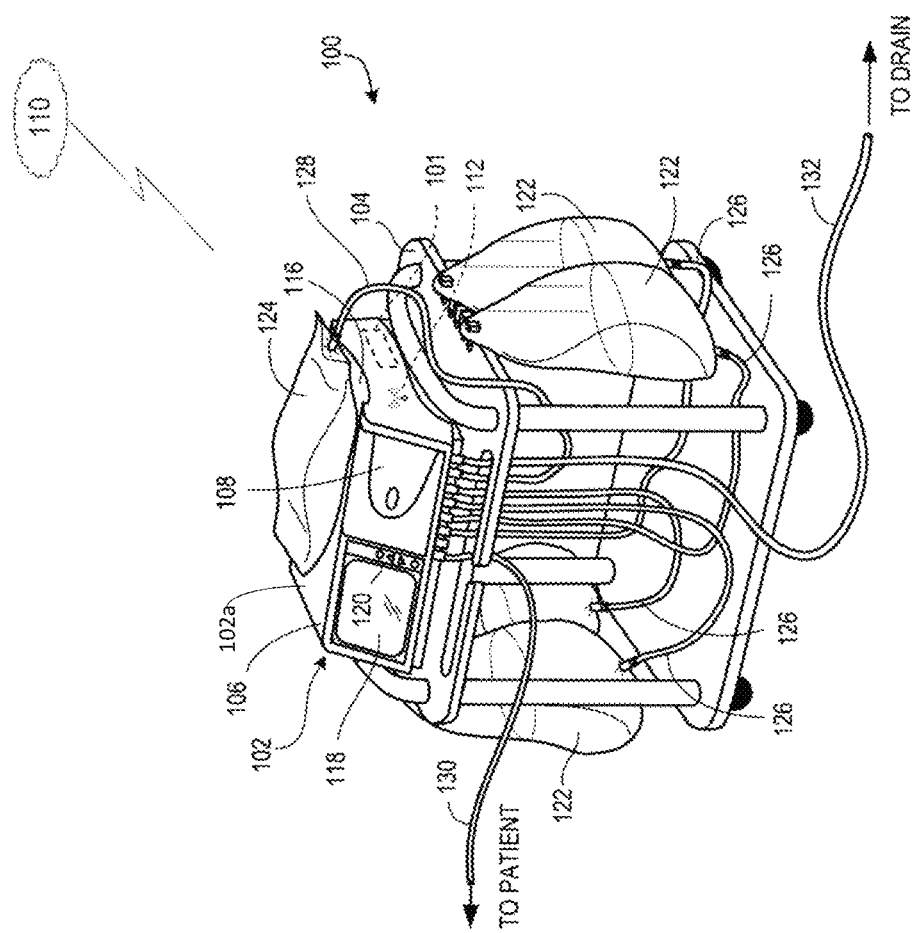
FIG. 1 illustrates an exemplary embodiment of a dialysis machine in a dialysis system configured in accordance with the present disclosure.

The present embodiments will now be described more fully hereinafter with reference to the accompanying drawings, in which several exemplary embodiments are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of dialysis machines and of methods for operating dialysis machines may minimize potential dialysate waste, e.g., so a patient may receive a fuller prescribed treatment, treatment times may be efficient, and use of the valuable treatment resources may be conserved and optimized to the benefit of the patient, hospital, dialysis centers, environment, etc. As described above, each dialysate bag may contain a volume of air (e.g., air content), which may be present as a result of the bag being not completely filled with dialysate during manufacture. Additionally, dialysate bags may be stored for a period of time prior to sale and/or use by a patient, e.g., 1-2 years or longer. Certain bag materials may be more susceptible to osmosis, for example, a Biofine™ material bag may have a greater volume of air content after a period of storage than a bag made of a different material, such as a polyvinyl chloride (PVC) material. For example, a bag may contain a range of approximately 20 cc to 150 cc of air. Although the term "bag" is used throughout, it should be understood that a dialysate bag may be any type of container capable of holding a fluid, e.g., a dialysate. In some embodiments, a fluid container may include a container in which dry concentrates are mixed with water to generate dialysate suitable for a dialysis treatment.

To ensure patient comfort and to efficiently receive the proper amount of dialysis treatment, air content in a dialysis treatment may be minimized by sensor detection and alarms. Additionally, a dialysis system may be primed, so that at a beginning of a treatment or beginning of delivery from each dialysate bag, prior to delivery of dialysate to a patient, a predetermined amount (e.g., 50 mL to 100 mL) of dialysate may be purged from the system so as to purge any air, for example, air content in the tubing and/or a pump cassette and/or initial air bubbles in dialysate bags/lines. This initial purge, or flush, may also help to remove potential contaminants that may be introduced at connections, e.g., between the bags and the lines, by flowing dialysate in a direction from the dialysate bag to the drain. When a predetermined volume of air is detected in the dialysate during treatment, or the system is primed, the dialysis machine may be configured to purge or drain waste instead of flowing the dialysate into a patient.

Heating the dialysate may present difficulties with managing temperature fluctuations in the dialysate (e.g., FIGS.

1-2), as well. For example, in dialysis machines having an internal heating element to heat a continuous flow of dialysate through a warmer pouch, if dialysate remains in or alongside a heating element for a time period longer than desired, such as if a kink in the tubing slows flow of dialysate through or by the heating element, the dialysate may become overheated (e.g., above approximately 98°-100° F., 37° C.). If the dialysate is overheated, it may be prevented from flowing into a patient so as to prevent discomfort or potential burning or other harmful effects. In some embodiments, if the dialysate is underheated (e.g., approximately 25° C.-33° C.), it may also be prevented from flowing into a patient until it has heated up to the desired temperature. For example, in batch heating embodiments a dialysate transfer may be delayed until the dialysate has been heated to a predetermined temperature. In in-line heating embodiments, underheated dialysate may be diverted and/or purged.

When air content is present in the dialysate or system, or the dialysate is at an unacceptable temperature, or another treatment event condition occurs where it is necessary for flow to the patient to be temporarily paused, the dialysate may be "temporarily unusable" for flowing into a patient. When temporarily unusable dialysate is dumped to drain, dialysate that was prescribed to the patient is wasted. Each event of temporarily unusable dialysate may result in a range of approximately 30 mL to 100 mL of dialysate being drained instead of flowing into a patient. As one to several events may occur in a single treatment, this wasted dialysate may result in a patient not receiving as full a prescribed treatment as might be possible, and treatment time and use of resources may not be optimal. It may therefore be advantageous as described herein to improve dialysate flow management to minimize or eliminate waste by instead of purging dialysate, diverting the temporary unusable dialysate to a dialysate container whereby it may be transferred to the patient for use later in the treatment.

FIG. 1 shows an example of a dialysis system 100 (e.g., a peritoneal dialysis (PD) system) that is configured in accordance with an exemplary embodiment of the system described herein. In some implementations, the dialysis system 100 may be configured for use at a patient's home (e.g., a home PD system). The dialysis system 100 may include a dialysis machine 102 (e.g., a peritoneal dialysis machine 102, also referred to as a PD cycler) and in some embodiments the machine may be seated on a cart 104. The dialysis machine 102 may include a housing 106, a door 108, and a cartridge interface for contacting a disposable cassette, or cartridge, where the cartridge is located within a compartment formed between the cartridge interface and the closed door 108. A heater tray 116 may be positioned on top of the housing 106. The heater tray 116 may be any size and shape to accommodate a bag of dialysate (e.g., a 5 L bag of dialysate) for batch heating. The dialysis machine 102 may also include a user interface such as a touch screen 118 and control panel 120 operable by a user (e.g., a caregiver or a patient) to allow, for example, set up, initiation, and/or termination of a dialysis treatment.

Dialysate bags 122 may be suspended from hooks the sides of the cart 104, and a heater bag 124 may be positioned in the heater tray 116. Hanging the dialysate bags 122 may improve air management as air content may be disposed by gravity to a top portion of the dialysate bag 122. Although four dialysate bags 122 are illustrated in FIG. 1, any number of dialysate bags may be connectable to the dialysis machine 102 (e.g., 1 to 5 bags, or more), and reference made to first and second bags is not limiting to the total number of bags used in a dialysis system 100. For example, the dialysis machine may have dialysate bags 122a, . . . 122n connectable in the system 101. In some embodiments, connectors and tubing ports may connect the dialysate bags 122 and lines for transferring dialysate. Dialysate from the dialysate bags 122 may be transferred to the heater bag 124 in batches. For example, a batch of dialysate may be transferred from the dialysate bags 122 to the heater bag 124, where the dialysate is heated by the heating element. When the batch of dialysate has reached a predetermined temperature (e.g., approximately 98°–100° F., 37° C.), the batch of dialysate may be flowed into the patient. The dialysate bags 122 and the heater bag 124 may be connected to the cartridge via dialysate bag lines or tubing 126 and a heater bag line or tubing 128, respectively. The dialysate bag lines 126 may be used to pass dialysate from dialysate bags 122 to the cartridge during use, and the heater bag line 128 may be used to pass dialysate back and forth between the cartridge and the heater bag 124 during use. In addition, a patient line 130 and a drain line 132 may be connected to the cartridge. The patient line 130 may be connected to a patient's abdomen via a catheter and may be used to pass dialysate back and forth between the cartridge and the patient's peritoneal cavity during use. The drain line 132 may be connected to a drain or drain receptacle and may be used to pass dialysate from the cartridge to the drain or drain receptacle during use (see FIGS. 4A-4B).

The touch screen 118 and the control panel 120 may allow an operator to input various treatment parameters to the dialysis machine 102 and to otherwise control the dialysis machine 102. In addition, the touch screen 118 may serve as a display. The touch screen 118 may function to provide information to the patient and the operator of the dialysis system 100. For example, the touch screen 118 may display information related to a dialysis treatment to be applied to the patient, including information related to a prescription.

The dialysis machine 102 may include a processing module 101 that resides inside the dialysis machine 102, the processing module 101 being configured to communicate with the touch screen 118 and the control panel 120. The processing module 101 may be configured to receive data from the touch screen 118 the control panel 120 and sensors, e.g., weight, air, flow, temperature, and/or pressure sensors, and control the dialysis machine 102 based on the received data. For example, the processing module 101 may adjust the operating parameters of the dialysis machine 102.

The dialysis machine 102 may be configured to connect to a network 110. The connection to network 110 may be via a wired and/or wireless connection. The dialysis machine 102 may include a connection component 112 configured to facilitate the connection to the network 110. The connection component 112 may be a transceiver for wireless connections and/or other signal processor for processing signals transmitted and received over a wired connection. Other medical devices (e.g., other dialysis machines) or components may be configured to connect to the network 110 and communicate with the dialysis machine 102.

Figure 2:
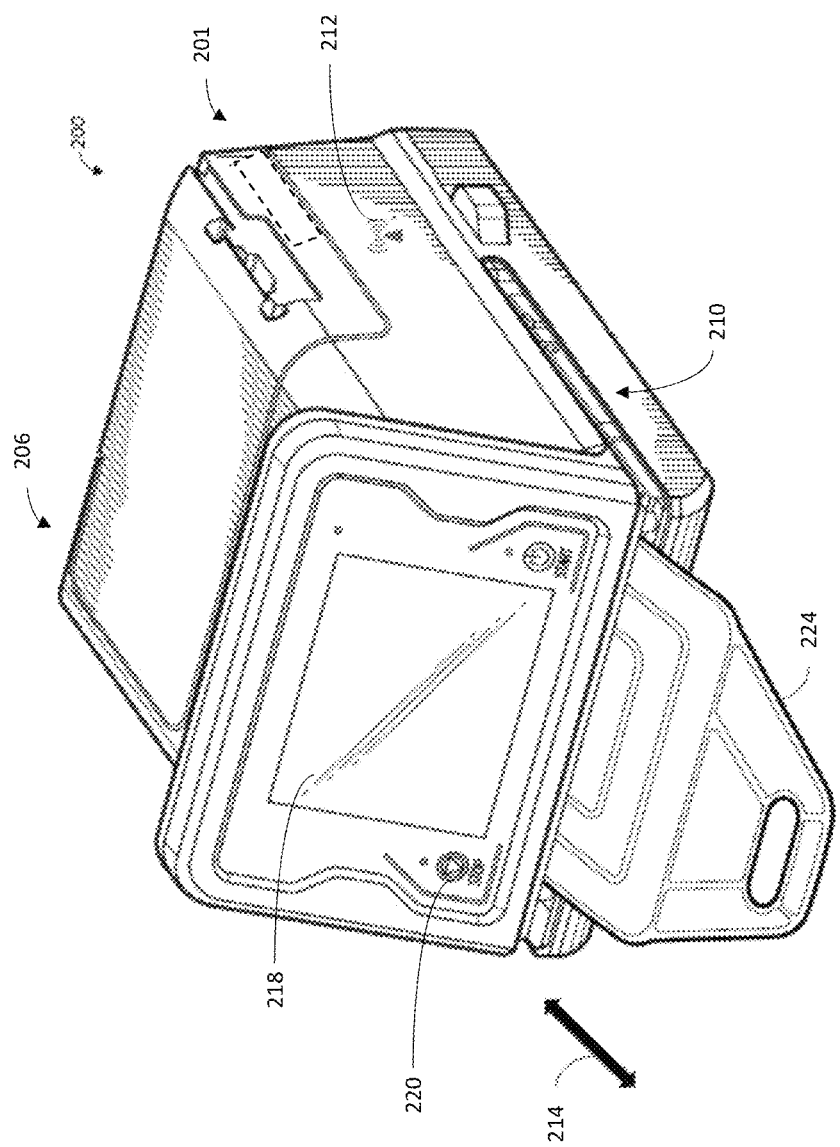
FIG. 2 illustrates another exemplary embodiment of a dialysis machine in accordance with the present disclosure.

Referring now to FIG. 2, another exemplary embodiment of a dialysis machine 200 in accordance with the present disclosure is shown. The dialysis machine 200 may be implemented in the peritoneal dialysis system 100 and may be in lieu of the dialysis machine 102, and may include, for example, a housing 206, a processing module 201, a connection component 212, a touch screen 218, and a control panel 220 operable by a user (e.g., a caregiver or a patient) to allow, for example, set up, initiation, and/or termination of a dialysis treatment. The processing module 201 and the connection component 212 may be configured similarly to the processing module 101 and connection component 112 described above. However, instead of a heater tray for a heater bag and batch heating being positioned on a top surface 102a of the housing as shown in FIG. 1, one or more heating elements may be disposed internal to the dialysis machine 200. For example, a warmer pouch 224 may be insertable into an opening 210 in a direction indicated at arrow 214. It is also understood that the warmer pouch 224 may be connectable to the dialysis machine 200 via tubing, or fluid lines, via a cartridge. The tubing may be connectable so that dialysate may flow from the dialysate bags 122, through the warmer pouch 224 for heating, and to the patient.

In such in-line heating embodiments, the warmer pouch 224 may be configured so dialysate may continually flow through the warmer pouch (instead of transferred in batches for batch heating) to achieve a predetermined temperature before flowing into the patient. For example, in some embodiments the dialysate may continually flow through the warmer pouch 224 at a rate between approximately 100-300 mL/min. Internal heating elements (not shown) may be positioned above and/or below the opening 210, so that when the warmer pouch 224 is inserted into the opening 210, the one or more heating elements may affect the temperature of dialysate flowing through the warmer pouch 224. In some embodiments, the internal warmer pouch may instead be a portion of tubing in the system that is passed by, around, or otherwise configured with respect to, a heating element(s).

In some embodiments, a dialysis machine 102, 200 may provide an active measurement of the dialysate temperature in dialysate bags, heater bag, and/or the warmer pouch e.g., in the dialysate bags 122, the heater bag 124, and/or the warmer pouch 224, or combinations thereof of FIGS. 1-2. It is understood that FIG. 1 illustrates that dialysate may be transferable to and stored in the heater bag 124 by "batch" until reaching an acceptable temperature for use, and that FIG. 2 illustrates dialysate continuously flowing through the warmer pouch 224 "in-line" with the dialysis machine 200, reaching an acceptable temperature by the application of internal heating elements.

As described above, embodiments having an in-line warmer pouch 224 may be more susceptible than embodiments utilizing batch heating to temperature variation of the dialysate. For example, if flow rate changes during treatment, such as a kink in the tubing occurring or an obstruction on the inlet, dialysate may dwell in the warmer pouch 224 for a longer time period and reach a higher than intended temperature. If dialysate is higher than approximately 41° C., or 105° F.-106° F., it may not be delivered to the patient to ensure patient safety.

Figure 3:
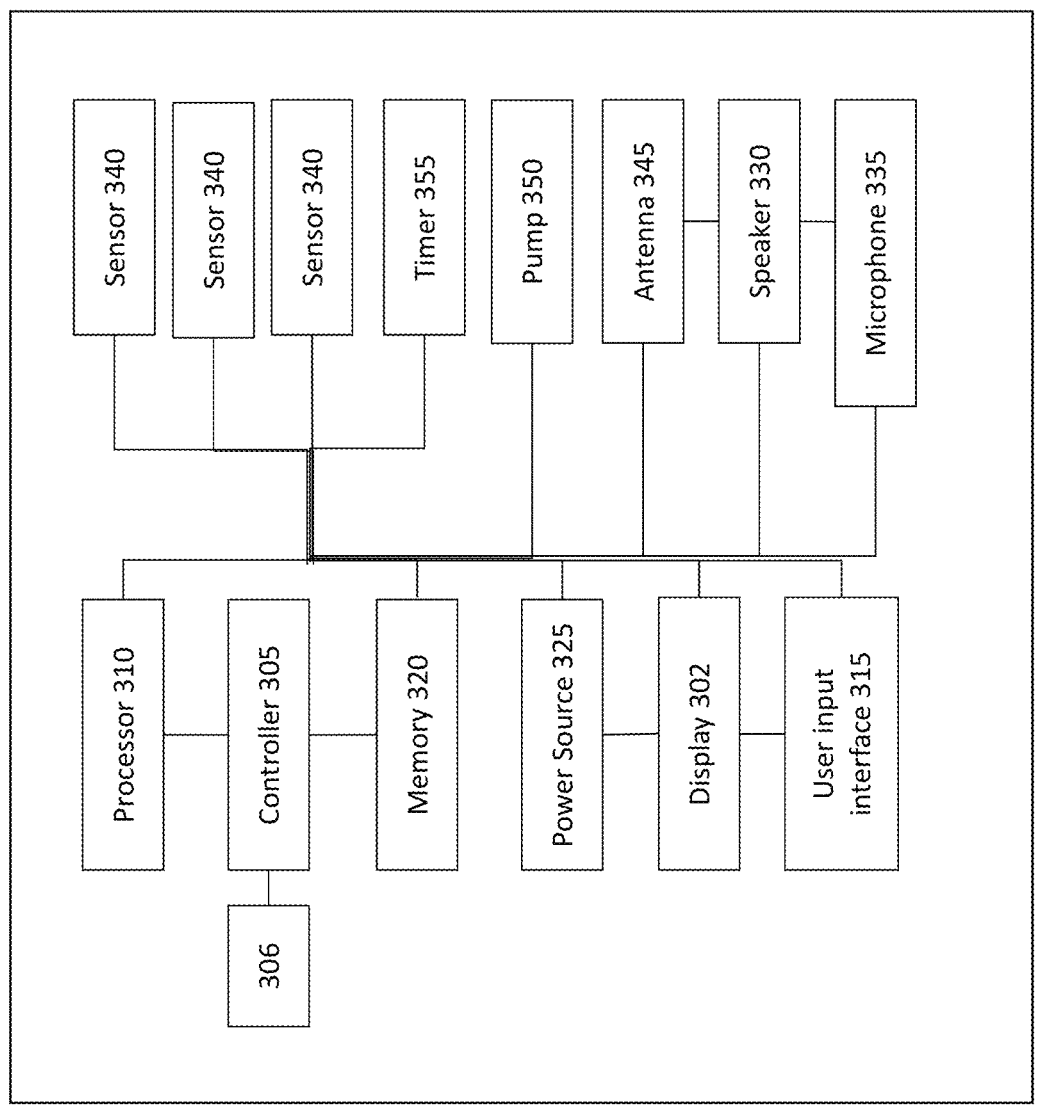
FIG. 3 is a block diagram illustrating an exemplary embodiment of a dialysis machine controller in accordance with the present disclosure.

Referring to FIG. 3, a schematic of an exemplary embodiment of a dialysis machine 300 and a controller 305 in accordance with the present disclosure are shown. The dialysis machine 300 may be a home dialysis machine, e.g., a peritoneal dialysis machine, for performing a dialysis treatment on a patient, and may be included in the system 100 for dialysis machines 102, 200, described above with respect to FIGS. 1-2 and dialysis machine 102, 200. Additionally, components described with respect to the dialysis machine 300 may also be included in the dialysis machines 102, 200. A power source 325 may provide power and/or a connection to an external power source to the dialysis machine 102, 200, 300, 405, 455.

Figure 4A:
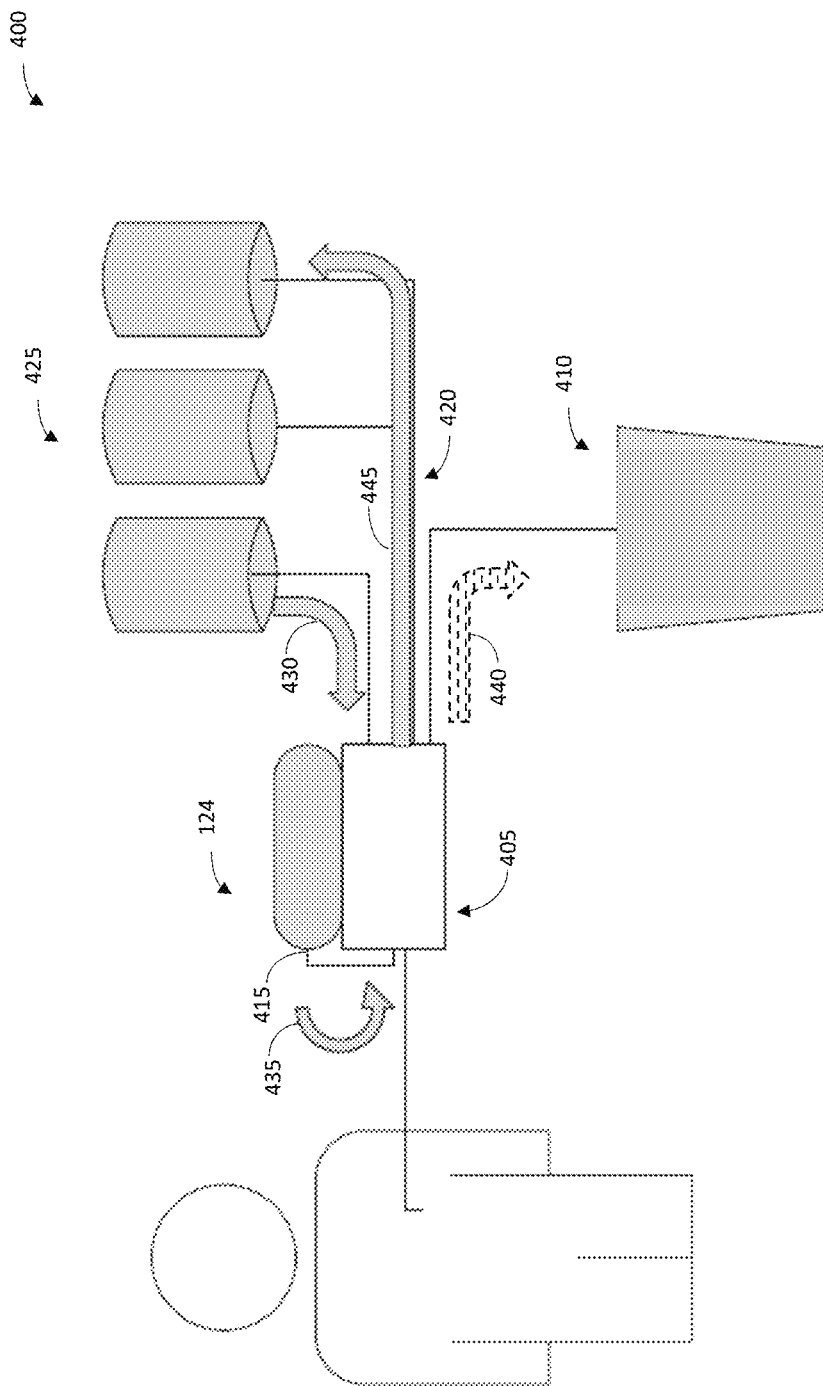
FIGS. 4A-4B illustrate exemplary embodiments of dialysis systems and methods for waste minimization of dialysis solution in accordance with the present disclosure.
Figure 4B:
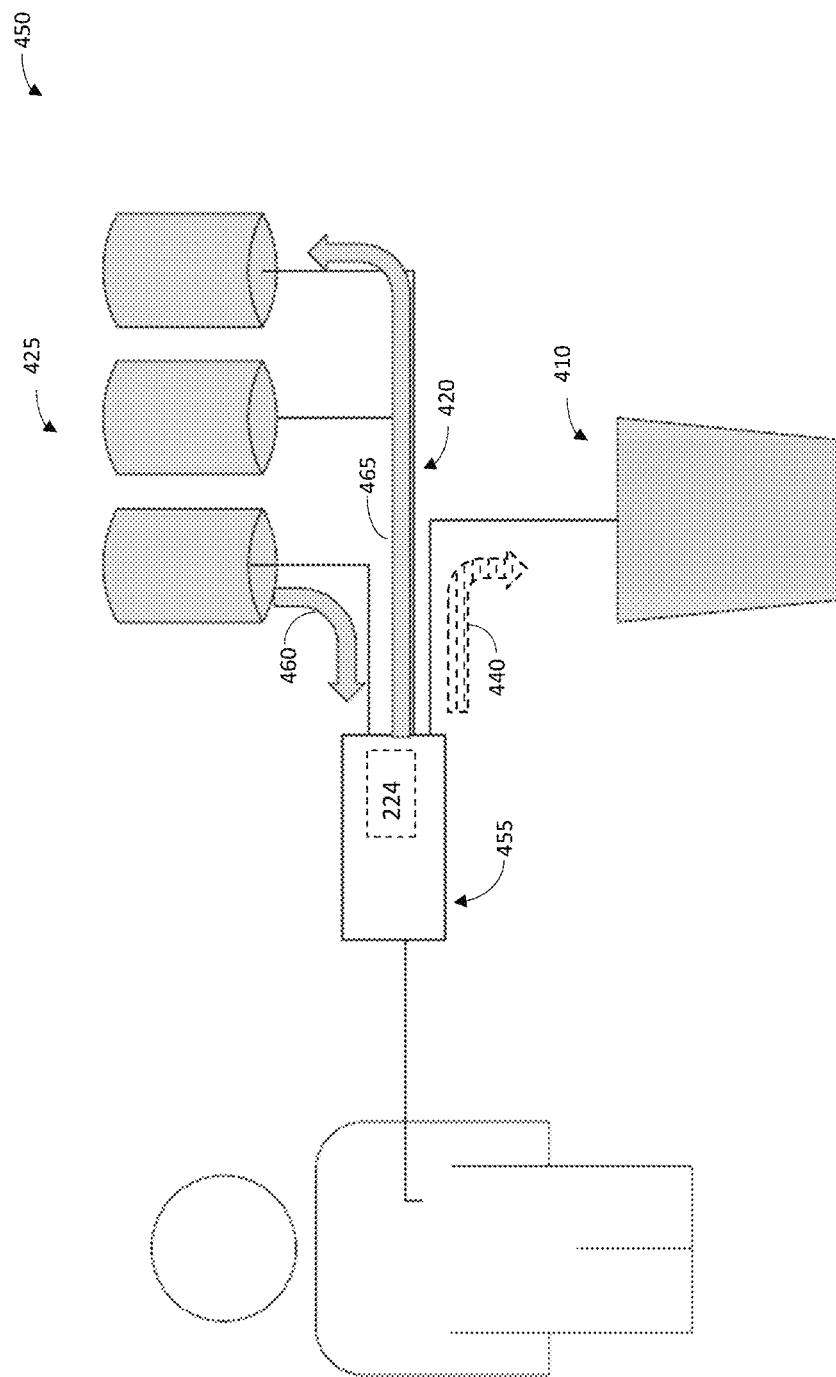
Figure 5:
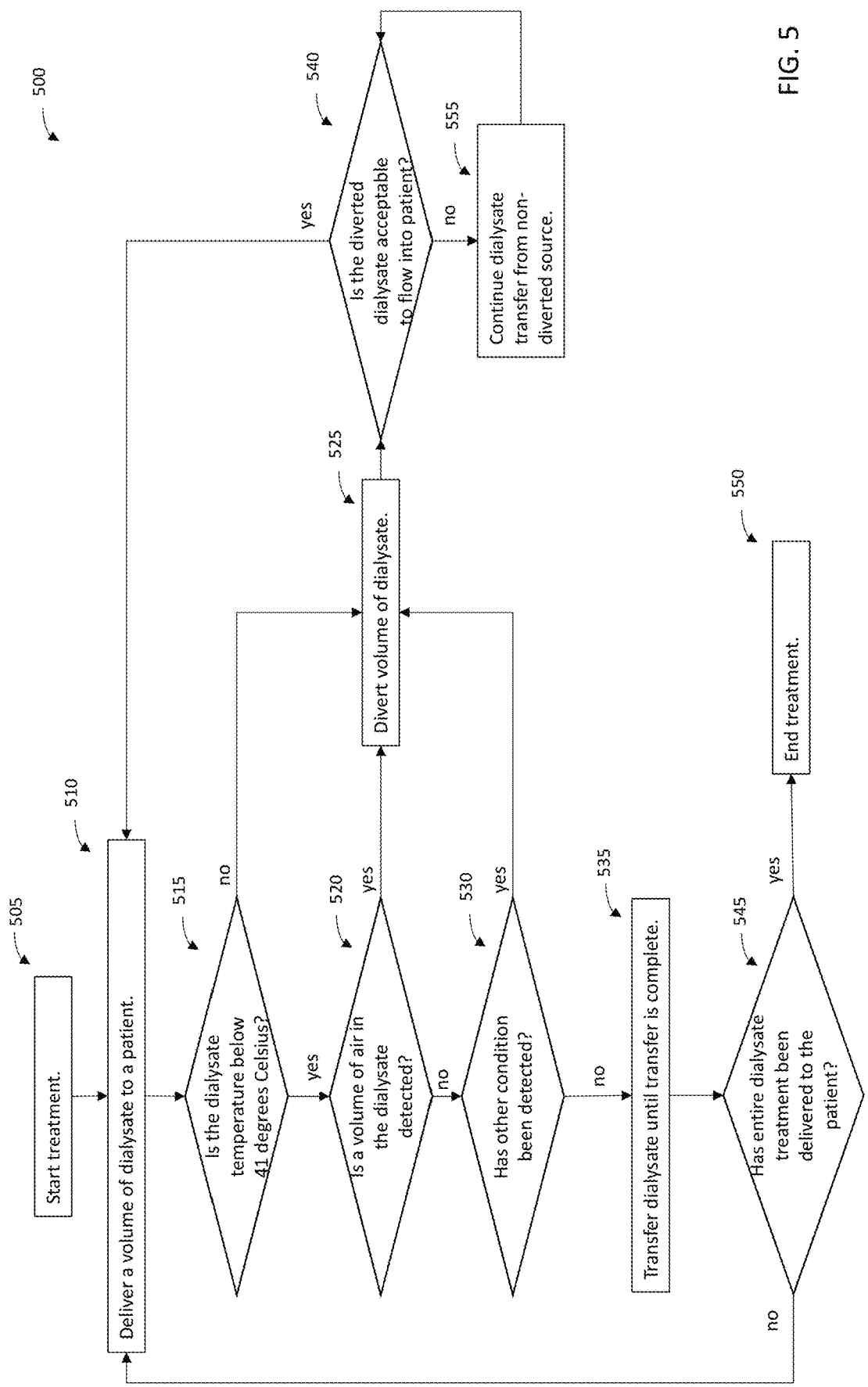
FIG. 5 is a flow diagram illustrating an exemplary embodiment of a dialysate system and method for waste minimization of dialysis solution for a dialysis machine in accordance with the present disclosure.

The controller 305 may automatically control execution of a treatment function during a course of dialysis treatment. For example, the controller 305 may control the delivery and transfer of dialysate as shown in FIGS. 4A-4B and FIG. 5 for dialysis machines 102, 200, 300, 405, 455. The controller 305 may be operatively connected to sensors 340 and deliver one or more signals to execute one or more treatment functions, or a course of treatment associated with various treatment systems. For example, dialysis treatment may include transferring dialysate from the dialysate bag 122 to the heater bag 124 and then to the patient, or delivering dialysate from the dialysate bag 122 through the warmer pouch 224 to the patient), or a course of treatment associated with various treatment systems. In some embodiments, a timer 355 may be included for timing triggering of sensors 340. It is understood that sensors, including but not limited to pressure sensors, weight sensors, flow sensors, air sensors, and temperature sensors, may detect dialysate temperature, fluid volume, air content, fluid flow rate, and fluid flow pressure for the dialysis machine 102, 200, 300, 405, 455 to determine flow delivery to and from the patient. For example, the dialysis machine 102, 200, 300, 405, 455 may include a plurality of sensors for detection and/or measurement of any combination of temperature, pressure, volume, air content, fluid flow. Multiple sensors may also be included to detect and/or measure individually the temperature, pressure, volume, air content, fluid flow.

In some embodiments, the controller 305, processor 310, and/or memory 320 of the dialysis machine 300 may receive sensor 340 signals indicating complete dialysate transfer of the dialysate bags, and indicating process parameters, such as temperature, pressure, air content, volume, flow rate, and the like. When either temperature and/or air content of the dialysate is at an unacceptable level, the controller 305, processor 310, and/or memory 320 may divert the temporarily unusable dialysate into a temporary holding container (e.g., an alternative dialysate bag) to be delivered to the patient later in the treatment. For example, each dialysate bag (e.g., the dialysate bags 122 and the heater bag 124) may contain an approximate amount of dialysate, such that "approximate amount" may be defined as a 3 L dialysate bag containing 3000 to 3150 mL, a 5 L dialysate bag containing 5000 to 5250 mL, and a 6 L dialysate bag containing 6000 to 6300 mL. Although bag volume is described herein as 3 L, 5 L and 6 L, it is understood that the specified volumes are only exemplary and bag volume may be any volume, and an "approximate" volume may be in a range within 10% of the desired volume. The controller 305 may also detect connection of all dialysate bags 122 connected. The controller 305 may monitor the dialysate bags 122 for dialysate transfer, so that the controller 305 knows the volume of dialysate that has been transferred from each dialysate bag 122, and if dialysate has been diverted to a dialysate bag 122 as a temporary holding container.

Communication between the controller 305 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

In embodiments, the dialysis machine 102, 200, 300 may include at least one pump 350 operatively connected to the controller 305. During a treatment operation, the controller 305 may control the pump 350 for pumping fluid, e.g., fresh and spent dialysate, to and from a patient. The pump 350 may also pump dialysate from the dialysate bag 122 to the heater bag 124, or to another dialysate bag 122. In embodiments where the warmer pouch 224 is in-line with the dialysis machine 200, the pump 350 may pump the dialysate through the warmer pouch 224 directly to the patient. The controller 305 may also be operatively connected to a speaker 330 and a microphone 335 disposed in the dialysis machine 300. A user input interface 315 may include a combination of hardware and software components that allow the controller 305 to communicate with an external entity, such as a patient or other user, and a display 302 may display information to the user or medical professional. These components may be configured to receive information from actions such as physical movement or gestures and verbal intonation. For example, the patient may enter via the user input interface 315 sizes of the dialysate bags 122 for use in treatment. In embodiments, the components of the user input interface 315 may provide information to external entities. Examples of the components that may be employed within the user input interface 315 include keypads, buttons, microphones, touch screens, gesture recognition devices, display screens, and speakers. The dialysis machine 102, 200, 300 may also be wirelessly connectable via the antenna 345 for remote communication.

As shown in FIG. 3, sensors 340 may be included for monitoring one or more parameters and may be operatively connected to at least the controller 305, processor 310, and memory 320. The processor 310 may be configured to execute an operating system, which may provide platform services to application software, e.g., for operating the dialysis machine 300. These platform services may include inter-process and network communication, file system management and standard database manipulation. One or more of many operating systems may be used, and examples are not limited to any particular operating system or operating system characteristic. In some examples, the processor 310 may be configured to execute a real-time operating system (RTOS), such as RTLinux, or a non-real time operating system, such as BSD or GNU/Linux.

According to a variety of examples, the processor 310 may be a commercially available processor such as a processor manufactured by INTEL, AMD, MOTOROLA, and FREESCALE. However, the processor 310 may be any type of processor, multiprocessor or controller, whether commercially available or specially manufactured. For instance, according to one example, the processor 310 may include an MPC823 microprocessor manufactured by MOTOROLA.

The memory 320 may include a computer readable and writeable nonvolatile data storage medium configured to store non-transitory instructions and data. In addition, the memory 320 may include a processor memory that stores data during operation of the processor 310. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 320 may include executable programs or other code that may be executed by the processor 310. The instructions may be persistently stored as encoded signals, and the instructions may cause the processor 310 to perform the functions described herein. The memory 320 may include information that is recorded, on or in, the medium, and this information may be processed by the processor 310 during execution of instructions. The memory 320 may also include, for example, specification of data records for user timing requirements, timing for treatment and/or operations, and historic sensor information. The medium may, for example, be optical disk, magnetic disk or flash memory, among others, and may be permanently affixed to, or removable from, the controller 305.

A pressure sensor may be included for monitoring fluid pressure of the dialysis machine 102, 200, 300, although the sensors 340 may also include any of a heart rate sensor, a respiration sensor, a temperature sensor, a flow sensor, a weight sensor, a video sensor, an air sensor, an air bubble sensor, a thermal imaging sensor, an electroencephalogram sensor, a motion sensor, audio sensor, an accelerometer, or capacitance sensor. In some embodiments, a flow sensor may detect and/or measure a flow of dialysate, e.g., to measure the dialysate transferred from the first and second bags to the patient. In some embodiments, a flow sensor may also detect and/or measure a flow of dialysate through the warmer pouch 224, or to the heater bag 124. It is appreciated that the sensors 340 may include sensors with varying sampling rates, including wireless sensors.

The controller 305 may be disposed in the dialysis machine 102, 200, 300 or may be coupled to the dialysis machine 102, 200, 300 via a communication port or wireless communication links, shown schematically as communication element 306 (see FIG. 3). According to various examples, the communication element 306 may support a variety of one or more standards and protocols, examples of which include USB, WiFi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the dialysis machine 300, the controller 305 may be operatively connected to any one or more of the sensors 340, pump 350, or combinations thereof. The controller 305 may communicate control signals or triggering voltages to the components of the dialysis machine 102, 200, 300. As discussed, exemplary embodiments of the controller 305 may include wireless communication interfaces. The controller 305 may detect remote devices to determine if any remote sensors are available to augment any sensor data being used to evaluate the patient.

Referring now to FIGS. 4A, 4B, and FIG. 5, an exemplary embodiment of a method for minimizing dialysate waste in accordance with the present disclosure is shown. FIG. 4A illustrates a dialysis system 400 including a dialysis machine 405 similar to the dialysis machine 102 in FIG. 1, including a heater bag 124 disposed on a heating element on a top of the dialysis machine 405. FIG. 4B illustrates a dialysis system 450 including a dialysis machine 455 similar to the dialysis machine 200 in FIG. 2, where the warmer pouch 224 is in-line with the dialysis machine 455. FIG. 5 shows an exemplary embodiment of a flow diagram of a method 500 for operating a dialysis machine, with a treatment beginning at step 505.

During treatment, a volume of dialysate may enter the patient's abdomen and remain for a period of time, e.g., a dwell time. During the dwell time, the dialysate may cause flow across the peritoneum of contaminants/toxins and/or particulates from a patient's blood and exchange substances and fluids (e.g., electrolytes, urea, glucose, albumin, osmotically active particles, and other small molecules). At the end of the dwell time, the used dialysate, ultrafiltrate, and/or contaminants/toxins may be flowed out of the patient's abdomen and purged to a drain 410 connected to the tubing 420, e.g., the drain line 132, indicated by arrow 440 and illustrated in dash-lines. This exchange of fresh dialysate and used dialysate after a dwell time may occur for several cycles depending on the patient's treatment regimen.

Both embodiments illustrated in FIGS. 4A and 4B may include dialysate containers 425, which in some embodiments may be dialysate bags 122 (see FIG. 1), where dialysate transfer between the respective dialysis machine and the dialysate bags 122 may be similar. In some embodiments, the dialysate container 425 may be an additional holding reservoir. The additional holding reservoir may be any type of a container, e.g., a bag, or other configuration for retaining dialysate, and/or for receiving diverted dialysate for later use in the treatment. In some embodiments, an additional holding reservoir may be configured in a similar manner to the dialysate bags 122. The additional holding reservoir, separate from the dialysate bags, may prevent mixing diverted dialysate with undelivered dialysate, although a separate additional holding reservoir may be optional. In some embodiments, separate additional holding reservoir may be advantageous to isolate detected air from dialysate. For example, diverting back into a dialysate bag 122 may reintroduce air for detection later in the treatment. Three dialysate containers 425 are shown merely for illustrative purposes, and it is understood that a treatment regimen may need more or less dialysate bags 122, and other dialysate containers may be connected to the dialysis machine 405, 455. It is understood that the individual patient treatment regimen and total dialysate volume in each bag may dictate how many dialysate bags 122 and/or other dialysate containers are connected to the dialysis machine 405, 455. For example, dialysate bags 122 may contain the same volume of dialysate, or a different volume of dialysate. Dialysate bags 122 may be sized to contain approximately 3 L, 5 L, and/or 6 L of dialysate. If a patient treatment regimen calls for 9 L total of dialysate, a patient may connect a 6 L dialysate bag and a 3 L dialysate bag to the dialysis machine 102. A dialysis treatment may include approximately 3 L-30 L of dialysate and may connect up to five bags to deliver the prescribed treatment.

At step 510, a volume of dialysate may be delivered to a patient. For example, dialysate may be delivered into the patient after being heated to a predetermined temperature via tubing 420. In batch heating embodiments, the dialysate may flow into the patient after heating to a predetermined temperature in the heater bag 124. In in-line heating embodiments, the dialysate may flow directly from dialysate bags to the patient by continuously flowing through the warmer pouch. The warmer pouch 224 may have a pathway for the dialysate to flow through, e.g., a tortuous or circuitous flow path, so that the dialysate may reach the predetermined temperature by the time the dialysate exits the flow path to continue into the patient. The dialysate may be heated up from room temperature to body temperature (approximately 98° F.-100° F., 37° C.) by batch or in-line heating, as described above. In some embodiments, tubing 420 may be fluid lines connecting a patient to the dialysis system via a cartridge, including but not limited to a dialysate bag lines 126, a heater bag line 128, a patient line 130, and a drain line 132. Additionally, it is also understood that for each treatment procedure, the patient receives a sterilized and disposable "set," including but not limited to tubing, a cartridge, dialysate bags, and the like. After each treatment, each "set" may be disposed of to minimize any potential contamination.

In embodiments, a volume of dialysate may be transferrable by batch to the heater bag 124 via the tubing 420 for heating before flowing into the patient, as shown in FIG. 4A and indicated by arrow 430. In other embodiments, a volume of dialysate may be transferrable through the warmer pouch 224 in-line with the dialysis machine 200 for heating before flowing into the patient, as shown in FIG. 4B and indicated by arrow 460. When the heater bag 124 is disposed above the dialysis machine 405 as illustrated in FIG. 4A, a batch of dialysate may flow from the heater bag 124 to the machine 405 indicated by arrow 435, e.g., to the cartridge for pumping into the patient. In other embodiments, as illustrated in FIG. 4B, when the warmer pouch 224 is in-line with the dialysis machine 455, extra steps may not be needed to flow the dialysate to the machine 455.

In some embodiments, e.g., illustrated in FIG. 4A, the dialysis machine 102, 405 may transfer an amount equal to a fill volume or a volume of the heater bag 124, plus an additional predetermined amount (e.g., 300 mL) in order to ensure sufficient dialysate volume for the next fill. However, air content may still be present in the heater bag 124. For example, the heater bag 124 may lie flat on the top surface 102a of the dialysis machine 102, 300, 405, 455 such that an air content contained in the heater bag 124 may migrate toward a side of the bag, possibly near a connection point 415 of the tubing 420. Some embodiments may account for this by tilting the top surface 102a, skewing the heater bag 124 to having a tubing connector at the lowest side to minimize air content (as air may flow up to an upper portion of the heater bag 124). However, this may not account for user set-up variability, e.g., home use possibly utilizing uneven surfaces. An alert or alarm, or multiple alerts or alarms, may be triggered by a detected air content even though a sufficient amount of dialysate is present.

At step 515, the dialysis machine 102, 200, 300, 405, 455 may determine whether a temperature of the dialysate is acceptable for delivery to the patient. In embodiments, a sensor 340 (e.g., a temperature sensor) may detect the dialysate temperature, and the processor 310 may compare the detected dialysate temperature to a predetermined maximum temperature. For example, the predetermined maximum temperature may be approximately 41° C. At step 520, the dialysis machine 102, 200, 300, 405, 455 may determine whether an air content (e.g., volume of air) is detected in the dialysate, and compare the detected air content to a predetermined maximum air content. In embodiments, another sensor 340 may detect air bubbles, a fluid pressure, or other value to determine if an unacceptable level of air is present. Unacceptable levels of air content may affect patient comfort during or after treatment.

If the dialysate temperature is acceptable at step 515, and/or an acceptable volume of air is detected in the dialysate at step 520, the dialysis machine 102, 200, 300, 405, 455 may determine if another condition has been detected that may necessitate dialysate diversion at step 530. This other condition may include detecting a new treatment set of a cartridge and tubing, priming the tubing, or detecting a treatment event alarm or flow stop, or combinations thereof. It is understood that the other condition may be an individual condition, multiples of an individual condition, or a combination of the conditions. In some embodiments, when a new treatment set of disposable bags, lines, cartridge, and the like, is introduced in the dialysis machine 102, 200, 300, 405, 455, the set may need to be primed, e.g., dialysate is flowed through to remove initial air content, to verify valves and connections, and the like. This may be a condition that generates an automatic signal when the new set is connected, for the dialysis machine to prime the set, or a user may manually initiate priming upon completion of set-up. In some embodiments, an event may occur during treatment, including but not limited to a kink in the tubing 420, a leak is detected, a contamination is detected, or combinations thereof, which may deviate from treatment protocol. It is understood that these events may be individual, or in combination with each other, or multiples of each event. In some embodiments, the treatment flow into the patient may be paused or stopped, and an alarm may signal to the user and/or a remote source, although dialysate may still be flowing through the set of tubing and the cartridge, and may still be heating. If no other condition is detected, then dialysate may be flowed into the patient at step 535. If another condition is detected, a condition signal may be generated and in response to the condition signal, the dialysate, a dialysate volume may be diverted as described below with respect to step 525.

It should be understood that steps 515, 520, and 530 may be performed in any order, or simultaneously, and may not be dependent on the outcome of the other. In embodiments, the dialysis machine 102, 200, 300, 405, 455 may perform only step 515 or multiple steps 515, only step 520 or multiple steps 520, only step 530 or multiple steps 530, or a combination of step 515, 520, and 530 or a combination of multiple steps 515, 520, and 530.

If a comparison of the detected dialysate temperature is above a predetermined temperature (e.g., approximately 41° C.) at step 515, a comparison of the air volume (e.g., air content) detected at step 520 is above a predetermined maximum air content, and/or another condition is detected to generate a signal (e.g., priming the set, a treatment event occurs), then the temporarily unusable dialysate volume may be diverted at step 525. In some embodiments, the volume of dialysate may be transferred to a dialysate container. For example, a dialysate container 425 may be dialysate bags 122, which may be unused dialysate bags from which dialysate has not yet been transferred or a used dialysate bag, or both, from which the dialysate has been transferred, where diverted dialysate is held in a dialysate bag 122 not currently being used by the dialysis machine 102, 200, 300, 405, 455. The dialysate container 425 may be an additional holding reservoir, separate from the dialysate bags 122 and configured for receiving diverted dialysate. The dialysate container 425 may act as a holding reservoir for diverted dialysate and allow the temporarily unusable dialysate to later be used in the treatment. For example, overheated dialysate may have time to cool (or may be actively cooled) to a temperature acceptable for delivering to the patient. Additionally, air bubbles may be allowed to converge and flow to an upper portion of the dialysate bag so that air content delivered may be minimized. The dialysis machine 102, 200, 300, 405, 455 may later be able to transfer the now-usable dialysate from the dialysate container 425 to the patient.

In some embodiments, the dialysate may passively cool to an acceptable temperature in the dialysate container 425, e.g., room temperature, through the course of treatment, although in other embodiments, the dialysis system may include an active cooling mechanism for the overheated dialysate. For example, the dialysate container 425 may be disposed adjacent to or coupled with an active cooling mechanism to actively lower the temperature of the diverted dialysate. The active cooling mechanism may include any one or a combination of a heat exchanger, a cooling element, a fan, a thermoelectric cooler (TEC), or the like.

In some embodiments, if the dialysate volume is diverted only for exceeding a predetermined temperature, the diverted dialysate may be flowed through an active cooling mechanism to lower the temperature of the dialysate, and then flowed to the patient. Instead of storing the diverted dialysate in a separate container, the dialysis system may continue to flow the diverted dialysate in parallel with dialysate flowing to the patient (e.g., via tubing 420) to the active cooling mechanism. Once the diverted dialysate is an acceptable temperature, the diverted dialysate may then be rejoined with dialysate flowing to the patient.

In embodiments, when dialysate is diverted from a first dialysate bag, the diverted dialysate may be transferred any other dialysate bag in which dialysate is not being immediately drawn or from which all dialysate has already been drawn, or which is specially designated as a holdover reservoir for diverted dialysate volumes. For example, FIG. 4A illustrates arrow 445 diverting dialysate into the farthest (from the dialysis machine 405) dialysate container 425 while dialysate is being drawn from the nearest (to the dialysis machine 405) dialysate container 425. Similarly, FIG. 4B illustrates arrow 465 diverting dialysate into the farthest (from the dialysis machine 455) dialysate container 425 while dialysate is being drawn from the nearest (to the dialysis machine 455) dialysate container 425.

In embodiments, the dialysis machine 102, 200, 300, 405, 455 may be configured to monitor which dialysate container 425 is flowing dialysate, and determine the dialysate container 425 to divert temporarily unusable dialysate. The diverted dialysate may be diverted to a single dialysate container 425, or a combination of multiple dialysate containers 425. In some embodiments, the dialysate container 425 to receive the diverted dialysate may be initially empty of dialysate, although in some embodiments, a volume of dialysate may be present. It may not be disadvantageous to mix, as fresh dialysate and diverted dialysate may be of the same concentrations. For example, in batch heating embodiments, dialysate from different dialysate containers 425 may be flowed into the heater bag 124, where it mixes together before flowing into the patient.

If the dialysate temperature is acceptable at step 515, no air content or an acceptable volume of air is detected in the dialysate at step 520, and/or no other condition is detected at step 530, the treatment may continue at step 535, exchanging fresh dialysate and used dialysate after a dwell time for a number of cycles dependent on the patient's treatment regimen. Dialysate may be transferred from all of the dialysate containers 425 (e.g., dialysate bags 122, heater bag 124, and/or warmer pouch 224, and dialysate container) connected to the dialysis machine 102, 200, 300, 405, 455 to complete a treatment. For example, in embodiments, the dialysis machine 102, 200, 300, 405, 455 may determine if the diverted dialysate volume is acceptable for use at step 540. A temperature sensor 340 may detect the temperature of the diverted dialysate, and a sensor 340 (e.g., a pressure sensor and/or weight sensor) may determine the air content present in the diverted dialysate volume. Other sensors 340, or a combination of temperature, pressure, weight, flow, and other sensors 340 may also be used in the dialysis machine 102, 200, 300, 405, 455 for detecting and monitoring the dialysate. If the diverted dialysate is acceptable for use, the dialysate volume may be delivered to the patient as in step 510. If the diverted dialysate volume is not acceptable for transfer to the patient, e.g., the dialysate temperature still exceeds approximately 41° C., an air content exceeds a predetermined maximum air content, then at step 555 the dialysis machine 102, 200, 300, 405, 455 may continue to hold the diverted dialysate volume and deliver dialysate from other non-diverted sources, e.g., dialysate bags 122. In embodiments, the dialysis machine 102, 200, 300, 405, 455 may include a timer 355 or other timing function to periodically check the diverted dialysate volume for acceptability. The timer 355 may be a predetermined time period, e.g., the diverted dialysate may be monitored in 5 or 10 minute intervals. In some embodiments, the diverted dialysate volume may be checked prior to diverting additional dialysate.

By diverting the temporarily unusable dialysate (e.g., overheated, containing air content or excess air content, initial dialysate flow for priming) to a dialysate container 425, it may be usable later in the treatment, thereby minimizing wasted dialysate. The dialysis machine 102, 200, 300, 405, 455 may determine at step 545 whether an entire dialysate treatment has been delivered to the patient. For example, the dialysis machine 102, 200, 300, 405, 455 may monitor levels of dialysate in all of the dialysate containers 425 throughout the treatment. For example, dialysate bags 122 may be completely transferred, either to the patient, or diverted to a dialysate container 425. As mentioned, multiple dialysate bags may be connectable to the dialysis machine 102, 200, 300, 405, 455 for delivering a prescribed treatment to a patient. Each dialysate bag may be transferred to the patient as described in co-pending application filed concurrently, entitled "Automatic Dialysate Detection in Dialysis Machines" to Plahey et al., which is herein incorporated by reference in its entirety.

If dialysate is diverted back into one of the dialysate bags 122, the dialysis machine 102, 200, 300, 405, 455 may ensure that the diverted dialysate may be delivered to the patient before the treatment ends at step 550, thereby ensuring the patient receives a more complete prescribed treatment. In embodiments where an additional holding reservoir is included, the dialysis machine 102, 200, 300, 405, 455 may first transfer dialysate from all of the dialysate bags 122. As described above, at step 540, if temporarily unusable dialysate was diverted to the additional holding reservoir, the dialysis machine 102, 200, 300, 405, 455 may determine if the temperature and air content are at acceptable levels so that the diverted dialysate may then be delivered to the patient.

Figure 6:
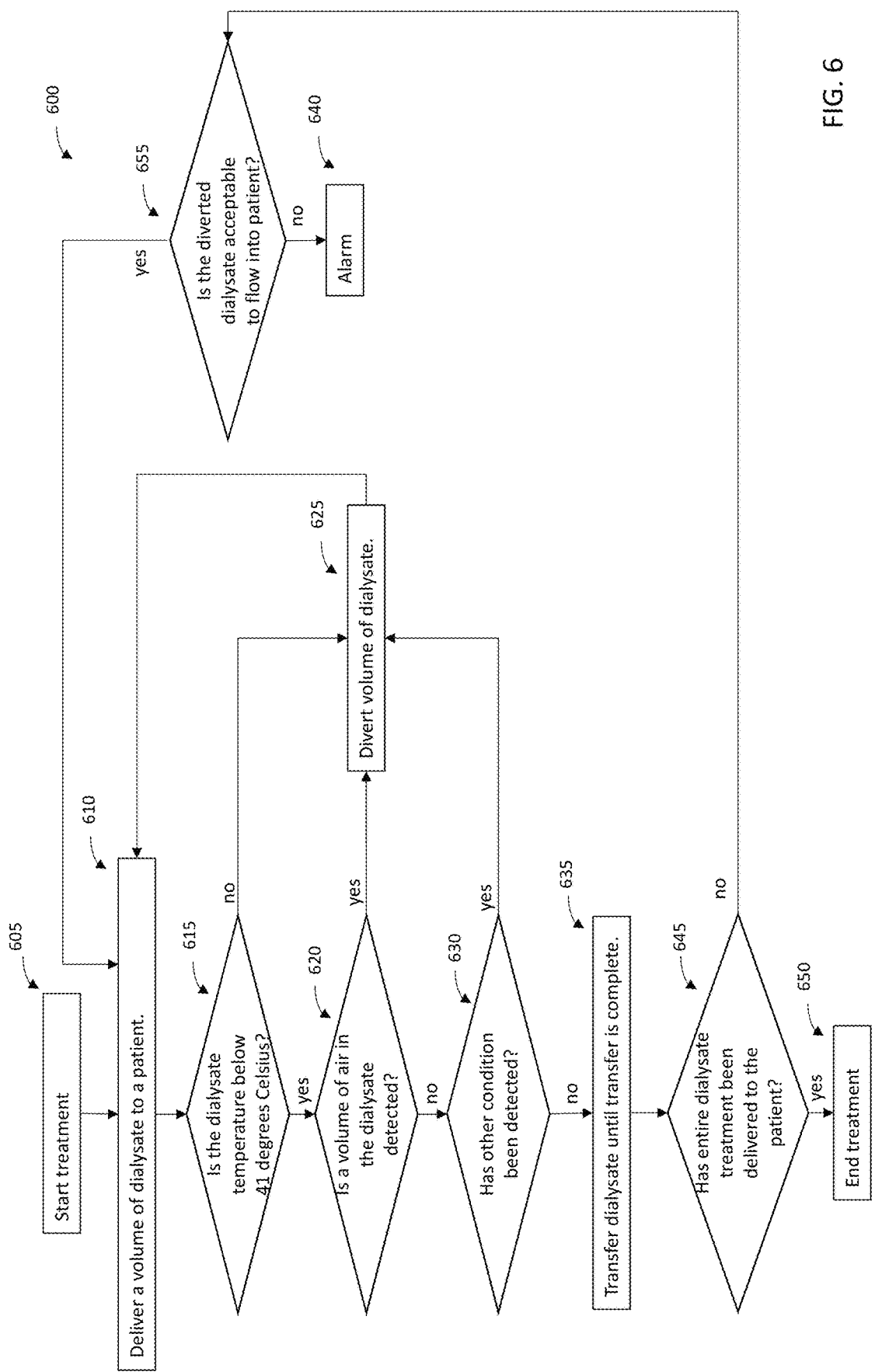
FIG. 6 is a flow diagram illustrating another exemplary embodiment of a dialysate system and method for waste minimization of dialysis solution for a dialysis machine in accordance with the present disclosure.

Referring now to FIG. 6, another exemplary embodiment of a system and method of delivering dialysate is shown. It is understood that steps 605, 610, 615, 620, 630, 635, 645, and 650 are identical to steps 505, 510, 515, 520, 530, 535, 545, and 550, respectively, as described above. In the flow diagram 600 of FIG. 6, instead of flowing the diverted dialysate as it is determined to be acceptable (e.g., decreases to an acceptable temperature), the diverted dialysate may be used after all the dialysate from dialysate bags 122 has been delivered to the patient.

As described above, if the dialysate temperature is above a predetermined temperature, e.g., 41° C. at step 615, if air is detected in the dialysate at step 620, or another condition has been detected at step 630, the volume of dialysate may be diverted at step 625. As mentioned, the dialysate may be diverted to an additional holding reservoir, or an unused dialysate bag, or a used dialysate bag, or combinations thereof. For example, the dialysis machine 102, 200, 300, 405, 455 may determine where to divert the dialysate based on the treatment cycle. When the dialysate has been diverted, the process may continue by returning to step 610, delivering another volume of dialysate to the patient, e.g., another cycle.

At step 645, the dialysis machine 102, 200, 300, 405, 455 may determine if the entire dialysate treatment has been delivered to the patient. If the total treatment volume has not been delivered to the patient, at step 655, the dialysis machine 102, 200, 300, 405, 455 may determine if the diverted dialysate is acceptable to flow into the patient, e.g., the diverted dialysate may be at an acceptable temperature for use. Air content may also converge to reduce air bubbles so less air may be delivered to the patient. If the dialysate is acceptable for the patient, the dialysis machine may continue by delivering the diverted dialysate at step 610. If the diverted dialysate is not acceptable for the patient to receive, the dialysis machine 102, 200, 300, 405, 455 may alarm. If a treatment volume delivered to the patient is less than a predetermined percentage of the total treatment volume, the dialysis machine 102, 200, 300, 405, 455 may alarm and may shut down without delivering any additional dialysate. For example, if the treatment volume delivered is less than 90% of the total treatment volume, the dialysis machine 102, 200, 300, 405, 455 may alarm or alert a user or medical professional that the treatment may be ineffective. In some embodiments, if a treatment volume delivered to the patient is less than a predetermined percentage of the total treatment volume, but greater than a minimum percentage of the total treatment volume, the dialysis machine may complete treatment but also generate an alarm or alert to notify the user or medical professional of the total treatment. For example, if the treatment volume delivered is greater than 90% of the total treatment volume, but less than 100%, the dialysis machine 102, 200, 300, 405, 455 may complete the treatment but also alert or alarm to notify the user or medical professional. Although the patient may receive an effective level of treatment, the alarm may alert the user to a condition of the dialysis machine 102, 200, 300, 405, 455 to address before beginning another treatment.

If at step 645 the dialysis machine 102, 200, 300, 405, 455 determines that the entire dialysate treatment has been delivered to the patient, the treatment may end at step 650.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or combinations thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A dialysis system for conducting a dialysis treatment, comprising:
    one or more dialysate containers arranged and configured to hold dialysate;
    a dialysis machine for transferring a volume of dialysate from the one or more dialysate containers to a patient;
    a dialysate reservoir container arranged and configured to receive diverted dialysate;
    wherein, the dialysis machine is configured to:
        flow the dialysate from the one or more dialysate containers to the patient;
        detect for the volume of the dialysate, a temperature of the dialysate volume, an air content of the dialysate volume, or another condition, or combinations thereof, wherein the detected temperature of the dialysate volume is compared to a predetermined maximum temperature, the detected air content of the dialysate volume is compared to a predetermined maximum air content, or the detected other condition generates a signal, or combinations thereof; and
        divert the volume of dialysate to the dialysate reservoir container in response to the detected temperature exceeding the predetermined maximum temperature, the air content exceeding the predetermined maximum air content, or the other condition generated signal, or combinations thereof;
        determine a total amount of the volume of dialysate delivered to the patient;
        determine if the diverted volume of dialysate is acceptable for delivery to the patient;
        in response to determining that the total amount of the volume of dialysate delivered to the patient is below a dialysate treatment volume and determining that the diverted volume of dialysate is acceptable for delivery, transferring the diverted volume of dialysate from the dialysate reservoir container to the patient; and
        in response to determining that the total amount of the volume of dialysate delivered to the patient is below a dialysate treatment volume and determining that the diverted volume of dialysate is unacceptable for delivery, transmitting an alarm or an alert.

2. The dialysis system of claim 1, further comprising a heater bag positioned on a top surface of the dialysis machine, the heater bag arranged and configured to change the volume of the dialysate from a first temperature to a second temperature, the second temperature being greater than the first temperature, wherein the volume of dialysate is deliverable from the one or more dialysate containers to the dialysis machine via the heater bag such that the dialysate is heatable by batch in the heater bag.

3. The dialysis system of claim 1, further comprising a warmer pouch insertable into the dialysis machine, the warmer pouch arranged and configured to receive the volume of dialysate from the one or more dialysate containers, the warmer pouch being arranged and configured to change the volume of dialysate from a first temperature to a second temperature, the second temperature being greater than the first temperature, wherein the volume of dialysate is delivered from the one or more dialysate containers to the dialysis machine via a warmer pouch.

4. The dialysis system of claim 3, wherein the warmer pouch is in-line with the dialysis machine, the warmer pouch being configured such that the dialysate is continuously flowable through the warmer pouch.

5. The dialysis system of claim 3, wherein the dialysis machine includes a slot, the warmer pouch being slideably insertable into the slot formed in the dialysis machine.

6. The dialysis system of claim 1, wherein the diverted volume of dialysate is deliverable to the patient after delivery of dialysate from all of the one or more dialysate containers.

7. The dialysis system of claim 1, wherein the diverted volume of dialysate is acceptable for delivery to the patient in response to the detected temperature being below the predetermined maximum temperature, the air content being below the predetermined maximum air content, or the other condition is acceptable, or combinations thereof.

8. The dialysis system of claim 1, wherein the dialysate reservoir container is an additional holding reservoir, an unused dialysate bag, or a used dialysate bag, or combinations thereof.

9. The dialysis system of claim 1, wherein the dialysis machine is configured to actively cool the volume of diverted dialysate.

10. The dialysis system of claim 1, wherein the dialysis machine is configured to provide an active measurement of the diverted dialysate.

11. The dialysis system of claim 1, wherein the other condition includes detecting a new treatment set of a cartridge and tubing, priming the tubing, or detecting a treatment event alarm or flow stop, or combinations thereof.

12. A dialysis system for conducting a dialysis treatment, comprising:
    one or more dialysate containers arranged and configured to hold dialysate;
    a dialysis machine for transferring a volume of dialysate from the one or more dialysate containers to a patient;
    a dialysate reservoir container arranged and configured to receive diverted dialysate;
    wherein, the dialysis machine is configured to:
        flow the dialysate from the one or more dialysate containers to the patient;

detect for the volume of the dialysate, a temperature of the dialysate volume, an air content of the dialysate volume, or another condition, or combinations thereof, wherein the detected temperature of the dialysate volume is compared to a predetermined maximum temperature, the detected air content of the dialysate volume is compared to a predetermined maximum air content, or the detected other condition generates a signal, or combinations thereof; and divert the volume of dialysate to the dialysate reservoir container in response to the detected temperature exceeding the predetermined maximum temperature, the air content exceeding the predetermined maximum air content, or the other condition generated signal, or combinations thereof;

determine a total amount of the volume of dialysate delivered to the patient;

determine if the diverted volume of dialysate is acceptable for delivery to the patient; and in response to determining that the total amount of the volume of dialysate delivered to the patient is below a dialysate treatment volume and determining that the diverted volume of dialysate is acceptable for delivery, transferring the diverted volume of dialysate from the dialysate reservoir container to the patient.

13. The dialysis system of claim 12, wherein in response to determining that the total amount of the volume of dialysate delivered to the patient is below a dialysate treatment volume and determining that the diverted volume of dialysate is unacceptable for delivery, transmitting an alarm or an alert.

14. The dialysis system of claim 12, wherein the diverted volume of dialysate is deliverable to the patient after delivery of dialysate from all of the one or more dialysate containers.

15. The dialysis system of claim 12, wherein the diverted volume of dialysate is acceptable for delivery to the patient in response to the detected temperature being below the predetermined maximum temperature, the air content being below the predetermined maximum air content, or the other condition is acceptable, or combinations thereof.

16. The dialysis system of claim 12, wherein the dialysate reservoir container is an additional holding reservoir, an unused dialysate bag, or a used dialysate bag, or combinations thereof.

17. The dialysis system of claim 12, wherein the dialysis machine is configured to actively cool the volume of diverted dialysate.

18. The dialysis system of claim 12, wherein the dialysis machine is configured to provide an active measurement of the diverted dialysate.

19. The dialysis system of claim 12, wherein the other condition includes detecting a new treatment set of a cartridge and tubing, priming the tubing, or detecting a treatment event alarm or flow stop, or combinations thereof.

20. The dialysis system of claim 12, further comprising a heater bag positioned on a top surface of the dialysis machine, the heater bag arranged and configured to change the volume of the dialysate from a first temperature to a second temperature, the second temperature being greater than the first temperature, wherein the volume of dialysate is deliverable from the one or more dialysate containers to the dialysis machine via the heater bag such that the dialysate is heatable by batch in the heater bag.

21. The dialysis system of claim 12, further comprising a warmer pouch insertable into the dialysis machine, the warmer pouch arranged and configured to receive the volume of dialysate from the one or more dialysate containers, the warmer pouch being arranged and configured to change the volume of dialysate from a first temperature to a second temperature, the second temperature being greater than the first temperature, wherein the volume of dialysate is delivered from the one or more dialysate containers to the dialysis machine via a warmer pouch.

22. The dialysis system of claim 21, wherein the warmer pouch is in-line with the dialysis machine, the warmer pouch being configured such that the dialysate is continuously flowable through the warmer pouch.

23. The dialysis system of claim 21, wherein the dialysis machine includes a slot, the warmer pouch being slideably insertable into the slot formed in the dialysis machine.

* * * * *